(12) United States Patent
Monsan et al.

(10) Patent No.: US 7,618,951 B2
(45) Date of Patent: Nov. 17, 2009

(54) USE OF PREBIOTICS, PREFERABLY GLUCOOLIGOSACCHARIDE, FOR THE PREVENTION OF THE ONSET OF TYPE II DIABETES

(75) Inventors: Pierre Monsan, Mondonville (FR); Philippe Valet, Toulouse (FR); Magali Remaud-Simeon, Ramonville-Saint-Agne (FR); Jean-Sebastien Saulnier-Blache, Balma (FR); Remy Burcelin, Ramonville-St Agne (FR)

(73) Assignee: Institut National de la Recherche Agronomique, Paris (FR)

( * ) Notice: Subject to any disclaimer, the term of this patent is extended or adjusted under 35 U.S.C. 154(b) by 284 days.

(21) Appl. No.: 10/527,819

(22) PCT Filed: Sep. 12, 2003

(86) PCT No.: PCT/FR03/02705

§ 371 (c)(1),
(2), (4) Date: Oct. 11, 2005

(87) PCT Pub. No.: WO2004/024167

PCT Pub. Date: Mar. 25, 2004

(65) Prior Publication Data

US 2006/0100172 A1    May 11, 2006

(30) Foreign Application Priority Data

Sep. 13, 2002   (FR) .................................. 02 11389

(51) Int. Cl.
*A61K 31/715*   (2006.01)
*A61K 31/702*   (2006.01)
*A61K 31/70*    (2006.01)
*A61K 31/7016*  (2006.01)

(52) U.S. Cl. .......................... 514/54; 514/53; 514/61; 514/23; 536/123.1; 536/123.13; 424/439

(58) Field of Classification Search .................. 514/54, 514/53, 23, 61; 536/123.1, 123.13; 424/439
See application file for complete search history.

(56) References Cited

U.S. PATENT DOCUMENTS

| | | | | |
|---|---|---|---|---|
| 4,001,435 A | * | 1/1977 | Hirao et al. ..................... | 426/3 |
| 4,518,581 A | * | 5/1985 | Miyake et al. ................. | 424/48 |
| 4,913,925 A | * | 4/1990 | Hiji ............................. | 426/599 |
| 4,978,397 A | * | 12/1990 | Carobbi et al. ............. | 127/46.2 |
| 5,817,634 A | | 10/1998 | Meezan et al. | |
| 5,981,510 A | | 11/1999 | Inada et al. | |

FOREIGN PATENT DOCUMENTS

| | | |
|---|---|---|
| DE | 199 61 182 | 6/2001 |
| EP | 0 325 872 | 8/1989 |
| EP | 1 156 057 | 11/2001 |
| EP | 1 332 759 | 8/2003 |

OTHER PUBLICATIONS

Roberfroid et al. (Annual Review of Nutrition, (1998) vol. 18, pp. 117-143).*
Letellier et al. (Canadian Journal of Veterinary Research = Revue Canadienne de Recherche Veterinaire, (Jan. 2000) vol. 64, No. 1, pp. 27-31) (Abstract Sent).*
Roberfroid M B: "Functional Foods: Concepts and Application to Inulin and Oligofructose" British Journal of Nutrition, Cambridge, GB, vol. 87, No. Suppl 2, May 2002, pp. S139-S143, XP009008910.
Chung C et al: "Glucooligosaccharides from Leuconostoc mesenteroides B-742, a potential prebiotic" Abstracts of the General Meeting of the American Society for Microbiology, vol. 101, 2001, p. 552, XP0009027712 & 101$^{st}$ General Meeting of the American Society for Microbiology, Orlando, FL, USA; May 20-24, 2001 ISSN: 1060-2011.
Boucher J et al: "Effect of non-digestible gluco-oligosaccharides on glucose sensitivity in high fat diet fed mice." Journal of Physiology and Biochemistry. Sep. 2003, vol. 59, No. 3, Sep. 2003, pp. 169-173, XP0009027711 ISSN: 1138-7548.
Roberfroid M B: "Prebiotics and probiotics: are they functional foods?" The American Journal of Clinical Nutrition. Jun. 2000, vol. 71, No. 6 Suppl, Jun. 2000, pp. 1682S-7S; disc, XP0001180260 ISSN: 0002-9165.

* cited by examiner

*Primary Examiner*—Shaojia Anna Jiang
*Assistant Examiner*—Michael C Henry
(74) *Attorney, Agent, or Firm*—Young & Thompson

(57) ABSTRACT

The invention relates to the use of prebiotics for the preparation of food or pharmaceutical compositions which are intended for the treatment and/or prevention of hyperglycaemic syndromes and, in particular, for the treatment of Type II diabetes and/or the prevention of the onset of Type II diabetes in patients with a predisposition to developing the type of diabetes. The invention also relates to the food and pharmaceutical compositions containing the prebiotics.

5 Claims, 2 Drawing Sheets intra-peritoneal glucose injection

USE OF PREBIOTICS, PREFERABLY GLUCOOLIGOSACCHARIDE, FOR THE PREVENTION OF THE ONSET OF TYPE II DIABETES

The subject of the present invention is the use of prebiotics for the treatment and prevention of hyperglycemic syndromes.

Prebiotics are non-digestible dietary compounds broken down by the micro-organisms of the intestinal flora and whose breakdown is responsible for benefits in the health of the host. The beneficial health effects are due to a selective stimulation of the growth and/or the biological activity of certain microorganisms of the intestinal flora, in particular the bifodobacteria and the lactic acid bacteria of the colic flora.

The effects of prebiotics are principally due to stimulation of the growth of bifidobacteria (bifidogenic effect). The stimulation of this growth allows a reduction in the pH of the colon, an increase in the production of short chain fatty acids, in particular butyrate and propionate, a prevention of the installation of pathogenic microorganisms (barrier effect), an increase in the metabolization of potentially carcinogenic aminated compounds and the production of vitamin B.

The use of prebiotics also allows stimulation of the immune system due to the production of lipoteichoic acid by the bacteria, the interaction of these bacteria with the Peyer's patches and the stimulation of peripheral lymphocyte circulation.

Prebiotics also encourage the digestive absorption of minerals, in particular calcium and magnesium, which allows their potential application in the context of the treatment of osteoporosis to be envisaged.

In the current situation the only prebiotics which are clearly defined are sugars classed among dietary fibres: non-digestible oligosaccharides (also called oligosides).

Oligosaccharides are monosaccharide polymers with a low degree of polymerization. The number of osidic units is typically from 2 to 12 units with an average of approximately 3-5 units. The monosaccharides involved in the formation of oligosaccharides are varied, in particular hexoligosides such as glucose, galactose, and fructose, but also pentoligosides such as xylose are found.

Oligosaccharides can be constituted by a single type of monosaccharide (homo-oligosides) or by a mixture (hetero-oligosides). The types of bonds between the osidic units are multiples: $\alpha(1\to 2)$, $\alpha(1\to 4)$, $\alpha(1\to 6)$, $\beta(1\to 4)$, $\beta(2\to 1)$.

Oligosaccharides can be derived: from the breakdown of natural polymers such as starch or inulin, from direct extractions from natural substances, such as soybean, or from chemical or enzymatic syntheses.

Glucooligosaccharides (glucooligosides) (GOS) constitute an important class of oligosaccharides. These are all of the oligosaccharides constituted by the chain formation of glucoligosides following the general formula (O-$\alpha$-D-gucopyranosyl)$_n$ where n is an integer from 2 to 10. It is possible to distinguish:

the maltooligosaccharides, originating from the hydrolysis of starch and corresponding to the general formula: [O-$\alpha$-D-gucopyranosyl-(1$\to$4)]$_n$ where n equals from 2 to 10, the isomaltooligosaccharides, also originating from the enzymatic conversion of starch hydrolysate and corresponding to the general formula [O-$\alpha$-D-gucopyranosyl-(1$\to$6)]$_n$ where n is an integer from 2 to 10, the oligodextrans comprising glucose (Glu) residues connected by bonds of the $\alpha(1\to 6)$ type and comprising at least one bond of the $\alpha(1\to 2)$ type. This type of polymer is obtained by enzymatic synthesis, in particular from maltose and saccharose in the presence of a glucosyl-transferase. The general formula of this type of compound is [Glu $\alpha(1\to 2)$][Glu $\alpha(1\to 6)$]$_n$[Glu $\alpha(1\to 4)$] Glu where n is an integer from 1 to 10 and the position of the $\alpha(1\to 2)$ bond is situated either at the non-reducing end, or is situated branched on the next-to-last glucose of the chain. The presence of this $\alpha(1\to 2)$ bond gives this oligosaccharide specific properties; in fact the human digestive system does not have the enzymatic means necessary for the hydrolysis of this type of bond. The stability of oligodextrans possessing this type of bond therefore allows them to be easily passed through, without being digested, into the large intestine where they can serve as a substrate specific for the colic microbial flora. These polymers therefore possess characteristics attaching them to prebiotics.

By way of example, GOS are more particularly described in the European patent application filed on $2^{nd}$ Aug. 1989, and published under the number 0 325 872.

Some studies on the interaction of oligosaccharides with the glucidic metabolism have been carried out on non-insulin dependent diabetics and on healthy subjects, and have demonstrated a possible impact on the glycoregulation. However, the effect of the prebiotic oligosaccharides on problems with the glucidic metabolism and their introduction in the subject presenting excess weight or obesity are not known.

Among the hyperglycemic syndromes, obesity-related type II diabetes, non-insulin-dependent diabetes mellitus, constitutes a growing public health problem in industrialized countries, largely because of the increased prevalence of obesity, itself due to a diet which is too rich.

The present invention results from the inventors demonstrating that mice subjected to a hyperlipidic diet and having received the administration of prebiotics not presenting the phenomenon of glucose intolerance that is detected in the group of control mice not treated with the prebiotics, and therefore that these mice treated with prebiotics behave like healthy individuals and do not develop type II diabetes, unlike the non treated group.

The present invention also results from the inventors demonstrating that the glycemia of mice suffering from type II diabetes could be reduced through a treatment based on prebiotics.

Thus the aim of the invention is principally to provide food, functional food, nutraceuticals or medicaments, intended for the treatment and/or the prevention of hyperglycemic syndromes and in particular for the treatment of type II diabetes and/or for the prevention of the appearance of type II diabetes in at-risk subjects.

For this purpose, a subject of the present invention is the use of prebiotics for the preparation of food or pharmaceutical compositions intended for the treatment and/or the prevention of hyperglycemic syndromes and in particular for the treatment of type II diabetes and/or for preventing the appearance of a type II diabetes in subjects presenting a predisposition to develop this type of diabetes, namely in subjects presenting clinical signs predictive of this diabetes, such as a decrease in glucose tolerance, or sensitivity to insulin, in particular in subjects presenting a hereditary predisposition to develop this type of diabetes, or linked to their eating habits, said subjects suffering from obesity, or being at risk of becoming obese.

By <<prebiotic>> is meant non-digestible dietary compounds whose beneficial effects on health are due to a selective stimulation of the growth and/or of the biological activity of certain bacteria of the intestinal flora.

By <<hyperglycemic syndrome>> is meant any pathology characterized by an abnormally high glycemia, i.e. any pathology characterized by a fasting glycemia greater than approximately 7.6 mmol/l. Hyperglycemic syndromes include in particular type I and II diabetes.

The subject of the invention is more particularly the above-mentioned use, of one or more prebiotics chosen from the compositions of non-digestible oligosaccharides comprising chain formations of identical or different monosaccharides, and whose degree of polymerization varies between 2 and 10, and preferably between 3 and 8.

Advantageously, the monosaccharides of the above-mentioned oligosaccharidic compositions are chosen from glucose, fructose, galactose, xylose, mannose, rhamnose and fucose.

The invention more particularly relates to the above-mentioned use of prebiotics chosen from:

glucooligosaccharides (GOS), namely glucose polymers of general formula [O-α-D-glucopyranosyl]$_n$ where n is an integer from 2 to 10, and preferably from 3 to 8, such as the polymers of general formula [O-α-D-glucopyranosyl-(1→2)][O-α-D-glucopyranosyl-(1→6)]$_n$[O-α-D-glucopyranosyl-(1→4)]O-D-glucopyranose where n is an integer from 1 to 10, and the position of the α(1→2) bond is situated either at the non-reducing end, or is branched on the next-to-last glucose of the chain, or the polymers of the maltooligosaccharide type of general formula [O-α-D-glucopyranosyl-(1→4)]$_n$ where n is an integer from 2 to 10, or the isomaltooligosaccharides of general formula [O-α-D-glucopyranosyl-(1→6)]$_n$ where n is an integer from 2 to 10, fructooligosaccharides (FOS) of general formula O-α-D-glucopyranosyl-(1→2)-[O-β-D-fructofuranosyl-(1→2)]$_n$ or [O-β-D-fructofuranosyl-(1→2)]$_m$ where n is an integer from 2 to 9, and m is an integer from 1 to 9, galactooligosaccharides of general formula O-α-D-glucopyranosyl-(1→4)-[O-β-D-galactopyranosyl-(1→6)]$_n$ where n is an integer from 2 to 5, xylooligosaccharides of general formula [O-β-xylofuranosyl-(1→4)]$_n$ where n is an integer from 2 to 9, soybean oligosaccharides such as raffinose of formula O-α-D-galactopyranosyl-(1→6)-O-α-D-glucopyranosyl-(1→2)-O-β-D-fructofuranoside and the stachyose of formula [O-α-D-galactopyranosyl-(1→6)]$_2$-O-α-D-glucopyranosyl-(1→2)-O-β-D-fructofuranoside, lactulose of formula O-β-D-galactopyranosyl-(1→4)-O-β-D-fructofuranose, lactosaccharose of formula O-β-D-galactopyranosyl-(1→4)-O-α-D-glucopyranosyl-(1→2)-O-β-D-fructofuranoside.

A subject of the invention is preferably the above-mentioned use of prebiotics chosen from glucooligosaccharides (GOS) as defined above, and more particularly GOS described in the European patent application filed on 2nd Aug. 1989, and published under the number 0 325 872.

For this purpose, a subject of the invention is more particularly the above-mentioned use of the following composition of glucooligosaccharides (GOS) (dry matter content):

fructose: less than 1%,
glucose: less than 4%,
disaccharides (maltose, leucrose, saccharose): from 9 to 11%,
trisaccharides (panose, maltotriose): from 9 to 11%,
GOS with a degree of polymerization 4: from 5 to 7%,
GOS* with a degree of polymerization 4: from 8 to 10%,
GOS with a degree of polymerization 5: from 18 to 22%,
GOS with a degree of polymerization greater than 5: from 36 to 44%, each GOS comprising a glycosidic α(1→2 bond) being situated either at the non-reducing end, or being situated branched on the next-to-last glucose of the chain, except the GOS* marked by an asterisk which does not contain any.

According to a particular embodiment, the GOS of the above composition correspond to the general formula [Glu α(1→2)][Glu α(1→6)]$_n$[Glu α(1→4)]Glu (n≧1), the glycosidic α(1→2) bond being situated either at the non-reducing end, or being situated branched on the next-to-last glucose of the chain, except for the GOS* (marked by an asterisk) which corresponds to the general formula [Glu α(1→6)]$_n$[Gluα(1→4)]Glu (n=2).

The invention also relates to the above-mentioned use of prebiotics as defined above, at a rate of approximately 10 to 30 g/day, up to approximately 100 g/day in the case of the use of GOS.

A subject of the invention is also the food compositions, nutritional additives, functional food, or nutraceuticals, comprising one or more prebiotics, and intended for the nourishment of subjects suffering from hyperglycemic syndrome and/or at risk of developing this syndrome, in the context of the treatment and/or the prevention of hyperglycemic syndromes, and in particular for the nourishment of subjects suffering from type II diabetes in the context of the treatment of this pathology and/or for the nourishment of subjects suffering from obesity, or at risk of becoming obese, and presenting a predisposition to develop this type of diabetes, namely in subjects presenting clinical signs predictive of this diabetes, such as a decrease in glucose tolerance, or sensitivity to insulin, in particular in subjects presenting a hereditary predisposition to develop this type of diabetes, or linked to their eating habits, in the context of preventing the appearance of a type II diabetes in these subjects.

For this purpose, the invention more particularly relates to the above-mentioned food compositions, nutritional additives, functional food or nutraceuticals, comprising one or more prebiotics chosen from the compositions of non-digestible oligosaccharides comprising chain formations of identical or different monosaccharides, and whose degree of polymerization varies between 2 and 10, and preferably between 3 and 8.

The invention more particularly relates to any food composition, nutritional additive, functional food or nutraceutical, as defined above, characterized in that the monosaccharides of the oligosaccharidic compositions are chosen from glucose, fructose, galactose, xylose, mannose, rhamnose and fucose.

A subject of the invention is also any food composition, nutritional additive, functional food or nutraceutical, as defined above, characterized in that the prebiotics are chosen from:

glucooligosaccharides (GOS), namely glucose polymers of general formula [O-α-D-glucopyranosyl]$_n$ where n is an integer from 2 to 10, and preferably from 3 to 8, such as the polymers of general formula [O-α-D-glucopyranosyl-(1→2)][O-α-D-glucopyranosyl-(1→6)]$_n$[O-α-D-glucopyranosyl-(1→4)]O-D-glucopyranose where n is an integer from 1 to 10, and the position of the α(1→2) bond is situated either at the non-reducing end, or is situated branched on the next-to-last glucose of the chain, or the polymers of the maltooligosaccharide type of general formula [O-α-D-glucopyranosyl-(1→4)]$_n$ where n is an integer from 2 to 10, or the isomaltooligosaccharides of general formula [O-α-D-glucopyranosyl-(1→6)]$_n$ where n is an integer from 2 to 10, fructooligosaccharides (FOS) of general formula O-α-D-glucopyranosyl-(1→2)-[O-β-D-fructofuranosyl-(1→2)]$_n$ or [O-β-D-fructofuranosyl-(1→2)]$_m$ where n is an integer from 1 to 9, and m is an integer from 2 to 9, galactooligosaccharides of general formula O-α-D-glucopyranosyl-(1→4)-[O-β-D-galactopyranosyl-(1→6)]$_n$ where n is an integer from 2 to 5, xylooligosaccharides of general formula [O-β-xylofuranosyl-(1→4)]$_n$ where n is an integer from 2 to 9, soybean oligosaccharides such as raffinose of formula O-α-D-galactopyranosyl-(1→6)-O-α-D-glucopyranosyl-(1→2)-O-β-D-fructofuranoside and stachyose of formula [O-α-D-galactopyranosyl-(1→6)]$_2$-O-α-D-glucopyranosyl-(1→2)-O-β-D-fructofuranoside, lactulose of formula O-β-D-galactopyranosyl-(1→4)-O-β-D-fructofuranose, lactosaccharose of formula O-β-D-galactopyranosyl-(1→4)-O-α-D-glucopyranosyl-(1→2)-O-β-D-fructofuranoside.

Food compositions, nutritional additives, functional food or nutraceuticals, as defined above, and which are preferred within the context of the present invention, are characterized in that the prebiotics are chosen from the above-mentioned glucooligosaccharides (GOS).

For this purpose, a subject of the invention is more particularly the food composition, nutritional additive, functional food or nutraceutical, as defined above, characterized in that the composition of glucooligosaccharides (GOS) is the following (dry matter content):
fructose: less than 1%,
glucose: less than 4%,
disaccharides (maltose, leucrose, sacharose): from 9 to 11%,
trisaccharides (panose, maltotriose): from 9 to 11%,
GOS with a degree of polymerization 4: from 5 to 7%,
GOS* with a degree of polymerization 4: from 8 to 10%,
GOS with a degree of polymerization 5: from 18 to 22%,
GOS with a degree of polymerization greater than 5: from 36 to 44%,
each GOS comprising a glycosidic α(1→2) bond being situated either at the non-reducing end, or being situated branched on the next-to-last glucose of the chain, except the GOS* marked by an asterisk which does not contain any.

According to a particular embodiment the GOS of the above composition correspond to the general formula [Glu α(1→2)][Glu α(1→6)]$_n$[Glu α(1→4)]Glu (n≧1), the glycosidic α(1→2) bond being situated either at the non-reducing end, or being situated branched on the next-to-last glucose of the chain, except for the GOS* (marked by an asterisk) which corresponds to the general formula [Glu α(1→6)]$_n$[Gluα (1→4)]Glu (n=2).

The invention also relates to any pharmaceutical composition which is characterized in that it comprises one or more prebiotics in combination with a pharmaceutically acceptable vehicle.

The invention more particularly relates to any pharmaceutical composition as defined above, characterized in that it comprises one or more prebiotics chosen from the compositions of non-digestible oligosaccharides comprising chain formations of identical or different monosaccharides, and whose degree of polymerization varies between 2 and 10, and preferably between 3 and 8.

A subject of the invention is more particularly any pharmaceutical composition as defined above, characterized in that the monosaccharides of the oligosaccharidic compositions are chosen from glucose, fructose, galactose, xylose, mannose, rhamnose and fucose.

Also, the invention more particularly relates to any pharmaceutical composition as defined above, characterized in that the prebiotics are chosen from:
glucooligosaccharides (GOS), namely glucose polymers of general formula [O-α-D-glucopyranosyl]$_n$ where n is an integer from 2 to 10, and preferably from 3 to 8, such as the polymers of general formula [O-α-D-glucopyranosyl-(1→2)][O-α-D-glucopyranosyl-(1→6)]$_n$[O-α-D-glucopyranosyl-(1→4)]O-D-glucopyranose where n is an integer from 1 to 10, and the position of the α(1→2) bond is situated either at the non-reducing end, or is situated branched on the next-to-last glucose of the chain, or the polymers of the maltooligosaccharide type of general formula [O-α-D-glucopyranosyl-(1→9)]$_n$ where n is an integer from 2 to 10, or the isomaltooligosaccharides of general formula [O-α-D-glucopyranosyl-(1→6)]$_n$ where n is an integer from 2 to 10, fructooligosaccharides (FOS) of general formula O-α-D-glucopyranosyl-(1→2)-[O-β-D-fructofuranosyl-(1→2)]$_n$ or [O-β-D-fructofuranosyl-(1→2)]$_m$ where n is an integer from 2 to 9, and m is an integer from 1 to 9, galactooligosaccharides of general formula O-α-D-glucopyranosyl-(1→4)-[O-β-D-galactopyranosyl-(1→6)]$_n$ where n is an integer from 2 to 5, xylooligosaccharides of general formula [O-β-xylofuranosyl-(1→4)]$_n$ where n is an integer from 2 to 9, soybean oligosaccharides such as raffinose of formula O-α-D-galactopyranosyl-(1→6)-O-α-D-glucopyranosyl-(1→2)-O-β-D-fructofuranoside and stachyose of formula [O-α-D-galactopyranosyl-(1→6)]$_2$-O-α-D-glucopyranosyl-(1→2)-O-β-D-fructofuranoside, lactulose of formula O-β-D-galactopyranosyl-(1→4)-O-β-D-fructofuranose, lactosaccharose of formula O-β-D-galactopyranosyl-(1→4)-O-α-D-glucopyranosyl-(1→2)-O-β-D-fructofuranoside.

A subject of the invention is more particularly any pharmaceutical composition as defined above, characterized in that the prebiotics are chosen from the above-mentioned glucooligosaccharides (GOS).

For this purpose, the invention more particularly relates to any pharmaceutical composition as defined above, characterized in that the composition of glucooligosaccharides (GOS) is as follows (dry matter content):
fructose: less than 1%,
glucose: less than 4%,
disaccharides (maltose, leucrose, sacharose): from 9 to 11%,
trisaccharides (panose, maltotriose): from 9 to 11%,
GOS with a degree of polymerization 4: from 5 to 7%,
GOS* with a degree of polymerization 4: from 8 to 10%,
GOS with a degree of polymerization 5: from 18 to 22%,
GOS with a degree of polymerization greater than 5: from 36 to 44%,
each GOS comprising a glycosidic α(1→2) bond being situated either at the non-reducing end, or being situated branched on the next-to-last glucose of the chain, except the GOS* marked by an asterisk which does not contain any.

According to a particular embodiment the GOS of the above composition correspond to the general formula [Glu α(1→2)][Glu α(1→6)]$_n$[Glu α(1→4)]Glu (n≧1), the glycosidic α(1→2) bond being situated either at the non-reducing end, or being situated branched on the next-to-last glucose of the chain, except for the GOS* (marked by an asterisk) which corresponds to the general formula [Glu α(1→6)]$_n$[Gluα (1→4)]Glu (n=2).

Advantageously the above-mentioned pharmaceutical compositions are in a form which can be administered by oral route.

Preferably, the above-mentioned pharmaceutical compositions are intended to be administered at a rate of approximately 10 to 30 g/day, up to approximately 100 g/day in the case of the use of GOS.

The invention is further illustrated by the following detailed description of the treatment and the prevention of the appearance of a type II diabetes in mice subjected to a hyperlipidic diet and treated with prebiotics as defined above.

EXAMPLES

Example 1

Prevention of the Appearance of Type II Diabetes by Chronic Treatment with GOS

I. Experimental Protocol

1. Appearance of Obesity 12 female mice C57B6 aged 8 weeks were subjected to a hyperlipidic diet for 20 weeks.

The food intake, provided ad libitum, comprised (in %):

|   |   |
|---|---|
| Corn starch: | 20 |
| Lard: | 20 |
| Casein: | 20 |
| Malto-dextrin: | 2 |
| Saccharose: | 22 |
| Cellulose: | 5 |
| Vitamins: | 1 |
| CM205b: | 7 |
| Soya bean oil: | 3 |

2. Chronic Treatment with Glucooligosaccharides (GOS)

The mice were separated into 4 groups of 3 mice comprising 2 groups of treated mice and 2 groups of control mice.

Throughout the period of the hyperlipidic diet the treated mice received in their drinking water 1.5 g/kg/d of a composition of glucooligosaccharides, i.e. 45 mg/d/mouse, which corresponds to the addition of I g of product per week and per cage in 100 mL of water.

The water intake and food intake were checked and the weight gain was measured each week.

The provided composition of glucooligosaccharide (BioEurope-Solabia) is as follows (content in % of dry matter):

| Sugar | Dry matter content (in %) |
|---|---|
| fructose | less than 1 |
| glucose | less than 4 |
| disaccharides (maltose, leucrose, saccharose) | from 9 to 11 |
| trisaccharides (panose, maltotriose) | 9 to 11 |
| GOS (d.p. 4) | 5 to 7 |
| GOS* (d.p. 4) | 8 to 10 |
| GOS (d.p. 5) | 18 to 22 |
| GOS (d.p. >5) | 36 to 44 |

The GOS used correspond to the general formula [Glu α(1 →2)] [Glu α(1 →6)]$_n$ [Glu α(1 →4)]Glu, the glycosidic α(1 →2) bond being situated either at the non-reducing end, or being situated branched on the next-to-last glucose of the chain, except for the GOS* (marked by an asterisk) which does not contain an α(1 →2) bond.

3. Measurements at 20 Weeks

Figure 1:
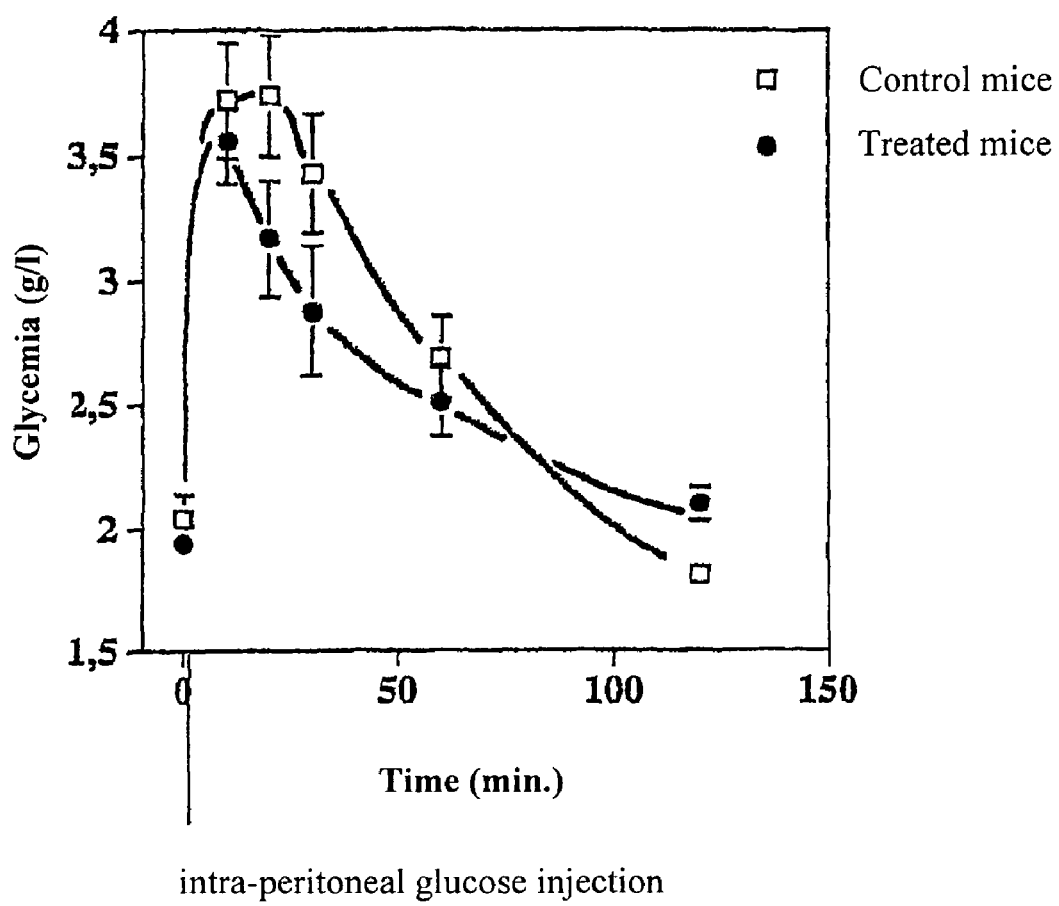
FIG. 1 The graph of the FIG. 1 represents the development of the glycemia (y-axis, g/l), as a function of time (x-axis, min.), following the intra-peritoneal injection of glucose (1 g/kg) to mice subjected to a hyperlipidic diet. The average values of the glycemia of 6 control mice are represented by white squares, the values corresponding to 6 mice whose diet was supplemented with GOS are represented by black circles.

At the end of the 20 weeks various measurements were carried out:

the urine was collected over 24 hours in order to measure the glucosuria using a Diabur-test 5000 device (Roche).

the fasting glycemia was measured using a Glucotrend plus apparatus (Roche)

the mice were subjected to a glucose tolerance test: intra-peritoneal injection of glucose at a rate of 1 g/kg and monitoring of the glycemia over 120 min. using a Glucotrendplus apparatus (Roche) (see FIG. 1).

after sacrifice of the mice the main tissues involved in glycoregulation (blood, liver, adipose tissue, muscle, kidney) were sampled.

II. Results

The tests carried out show that the excess weight of the control and treated animals are similar and the fatty deposits are equivalent. Moreover the glucosuria and the fasting glycemia are normal, which indicates that obesity-related diabetes has not appeared. The glucose tolerance test (FIG. 1) by contrast indicates that the control mice present a glucose resistance while this phenomenon is significantly corrected in the treated mice.

Glucose intolerance is considered to be one of the first symptoms of the appearance of type II diabetes. It therefore appears that the treatment with glucooligosaccharides is sufficient to prevent the appearance of this diabetes in a murine obesity model.

Example 2

Treatment of Type II Diabetes by Acute Treatment with GOS

I. Experimental Protocol

1. Appearance of Type II Diabetes 30 male mice C57B6 aged 12 weeks were subjected to a hyperlipidic diet for 8 weeks.

The food intake, provided ad libitum, comprised (in %):

| | |
|---|---|
| Casein: | 37 |
| Cellulose: | 10 |
| Vitamins: | 1 |
| Corn oil: | 14.5 |
| Lard: | 35 |
| Mineral salts: | 2.5 |

The appearance of type II diabetes was verified by measurement of the fasting glycemia as well as by a glucose tolerance test, according to the procedures described in Example 1.

2. Acute Treatment with Glucooligosaccharides (GOS)

The diabetic mice were separated into 2 groups of 15 mice each. The first group were treated with an oral administration of 1.5 g/kg of a composition of GOS identical to that used in Example 1, the second group did not receive GOS. 15 minutes later, an oral administration of 1 g/kg of glucose was carried out for the two groups. The glycemia was measured before the administration of GOS (−15 min.), before that of glucose (0 min.), then at times 15, 30 and 60 min. after the administration of glucose (see FIG. 2)

II. Results

Figure 2:
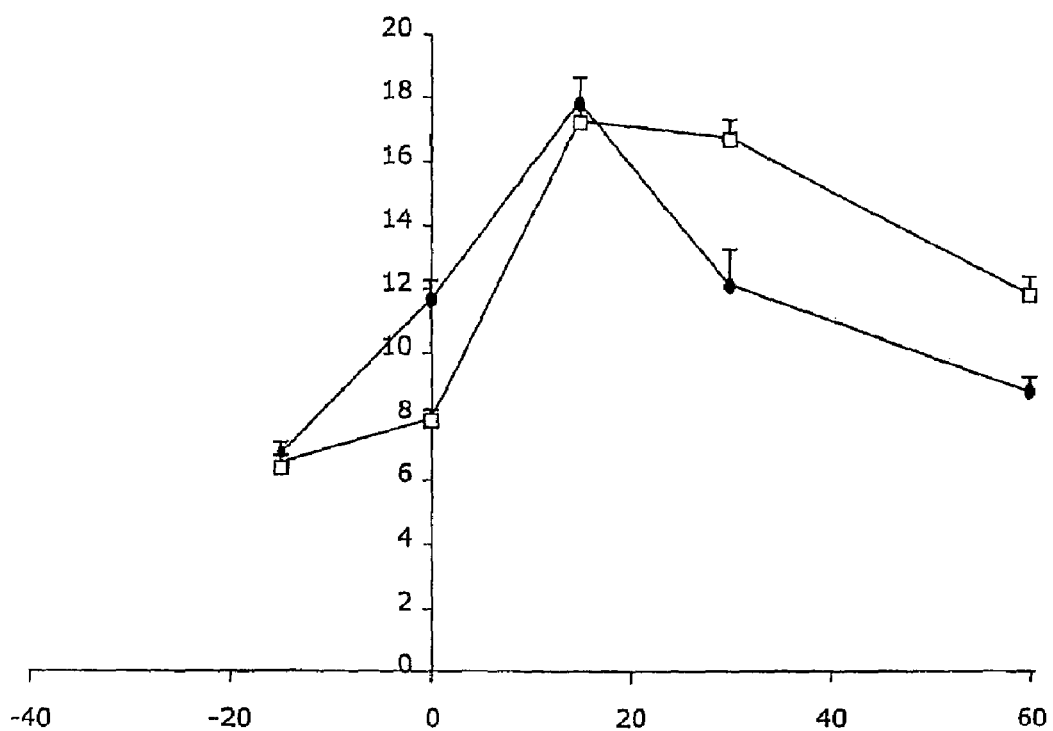
FIG. 2 The graph of FIG. 2 represents the development of the glycemia (y-axis, mM), as a function of time (x-axis, min.), following the oral administration of glucose (1 g/kg, time 0 min.) to mice suffering from type II diabetes. The average values of the glycemia of 15 control mice are represented by white squares, the values corresponding to 15 mice to which GOS has been administered (time −15 min.) are represented by black circles.

The oral administration of the mixture of GOS induces a more rapid and more marked decrease in the significant glycemia 30 min. after the administration of glucose (FIG. 2). The oral administration of a mixture of GOS reduces the glucose intolerance of the diabetic mice.

Consequently, in addition to their role in the prevention of the appearance of type II diabetes, it appears that the GOS allow a reduction of the glycemia in a murine model of type II diabetes.

The invention claimed is:

1. A method for treating hyperglycemic syndrome and/or type II diabetes in a subject, comprising: administering to a subject in need thereof an effective amount of prebiotic non-digestible oligosaccharides comprising glucooligosaccharides (GOS) whose degree of polymerization is from 2 to 10, the composition of said glucooligosaccharides (GOS) being as follows (dry matter content):
less than 1% fructose,
less than 4% glucose,
9-11% disaccharides wherein at least one disaccharide is selected from the group consisting of maltose, leucrose, and sacharose,
9-11% trisaccharides selected from the group consisting of panose and maltotriose,
5 to 7% GOS with a degree of polymerization 4,
8 to 10% GOS* with a degree of polymerization 4,
18 to 22% GOS with a degree of polymerization 5,
36 to 44% GOS with a degree of polymerization greater than 5, and
wherein each GOS comprises a glycosidic $\alpha(1\rightarrow2)$ bond at its non-reducing end or carried by the next-to-last glucose, with the exception of GOS* which does not contain any.

2. The method according to claim 1, wherein prebiotics comprising GOS are administered at a rate of 1.5 g/kg/day or a rate of approximately 10 to 30 g/day.

3. A food composition, nutritional additive, functional food or nutraceutical for the nourishment of subject having hyperglycemic syndrome and/or type II diabetes in a subject, comprising one or more prebiotics wherein said prebiotics are compositions of non-digestible oligosaccharides comprising chain formations of identical or different monosaccharides, whose degree of polymerization varies from 2 to 10, and whose monosaccharides are selected from the group consisting of glucose, fructose, galactose, xylose, mannose, rhamnose and fucose,
wherein a food composition comprising a mixture of isomaltotriose, isomaltotetraose and isomaltopentose is excluded,
wherein fructooligosaccharides are excluded,
wherein the prebiotics are glucooligosaceharides (GOS), the composition of said glucooligosaceharides (GOS) being as follows (dry matter content):
fructose: less than 1%,
glucose: less than 4%,
disaccharides where at least one of said disaccharides is selected from the group consisting of maltose, leucrose, and sacharose : from 9 to 11%,
trisaccharides where at least one of said trisaccharides consisting of panose, or maltotriose: from 9 to 11%,
GOS with a degree of polymerization 4: from 5 to 7%,
GOS* with a degree of polymerization 4: from 8 to 10%,
GOS with a degree of polymerization 5: from 18 to 22%,
GOS with a degree of polymerization greater than 5: from 36 to 44%, and
wherein each GOS comprises a glycosidic $\alpha(1\rightarrow2)$ bond at its non-reducing end or is carried by the next-to-last glucose, except GOS* does not contain any.

4. A pharmaceutical composition comprising a pharmaceutically acceptable vehicle, one or more prebiotics, said prebiotics being compositions of non-digestible oligosaccharides comprising chain formations of identical or different monosaccharides, whose degree of polymerization varies from 2 to 10, and whose monosaccharides are selected from the group consisting of glucose, fructose, galactose, xylose, mannose, rhamnose and fucose,
wherein fructooligosaccharides are excluded,
wherein the prebiotics are glucooligosaccharides (GOS) and the composition of said glucooligosaccharides (GOS) are as follows (dry matter content):
fructose: less than 1%,
glucose: less than 4%,
disaccharides wherein at least one of said disaccharides is selected from the group consisting of maltose, leucrose, and sacharose : from 9 to 11%,
trisaccharides wherein at least one of said trisaccharides is panose, or maltotriose: from 9 to 11%,
GOS with a degree of polymerization 4: from 5 to 7%,
GOS* with a degree of polymerization 4: from 8 to 10%,
GOS with a degree of polymerization 5: from 18 to 22%,
GOS with a degree of polymerization greater than 5: from 36 to 44%, and wherein each GOS comprises a glycosidic $\alpha(1\rightarrow2)$ bond at its non-reducing end or carried by the next-to-last glucose, except GOS* does not contain any.

5. A composition, comprising:
prebiotic glucooligosaccharides (GOS) on a dry matter basis as follows:
less than 1% fructose,
less than 4% glucose,
9-11% disaccharides wherein at least one disaccharide is selected from the group consisting of maltose, leucrose, and sacharose,
9-11% trisaccharides selected from the group consisting of panose and maltotriose,
5 to 7% GOS with a degree of polymerization 4, 8 to 10% GOS* with a degree of polymerization 4,
18 to 22% GOS with a degree of polymerization 5,
36 to 44% GOS with a degree of polymerization greater than 5, and wherein each GOS comprises a glycosidic $\alpha(1\rightarrow2)$ bond at the non-reducing end or at the next-to-last glucose, with the exception of GOS* which does not contain a glycosidic $\alpha(1\rightarrow2)$ bond.

* * * * *